Figure 1:
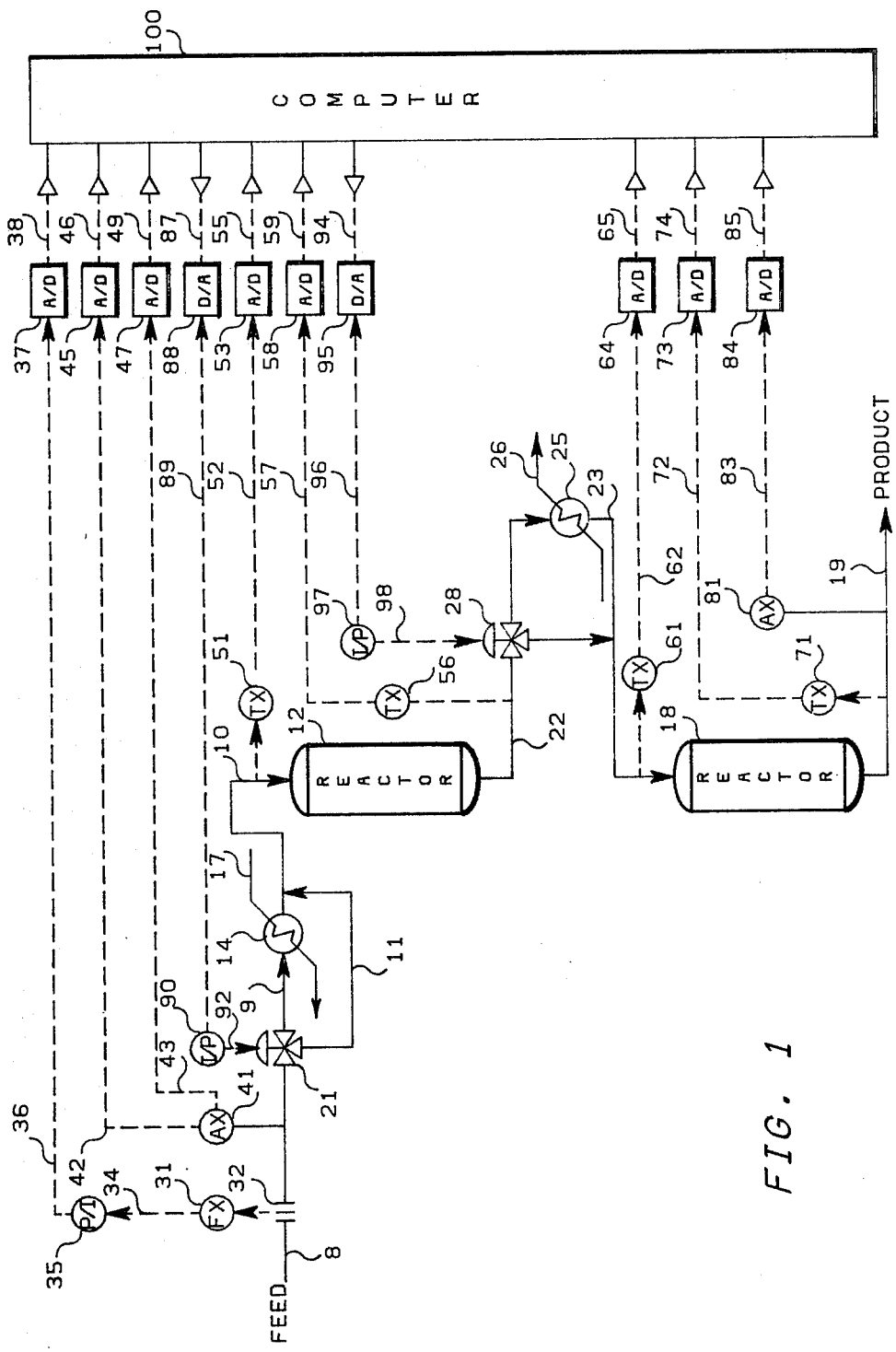

United States Patent

Funk

[11] 4,249,908
[45] Feb. 10, 1981

[54] TEMPERATURE CONTROL OF EXOTHERMIC REACTIONS

[75] Inventor: Gary L. Funk, Bartlesville, Okla.

[73] Assignee: Phillips Petroleum Company, Bartlesville, Okla.

[21] Appl. No.: 74,274

[22] Filed: Sep. 11, 1979

[51] Int. Cl.³ .............................................. C07B 1/00
[52] U.S. Cl. .................................. 23/230 A; 260/690; 260/698; 260/700; 364/500; 364/557; 422/62; 585/259; 585/263
[58] Field of Search .................. 422/62, 105, 108, 110; 23/230 A; 260/690, 698, 700; 585/259, 263; 364/500, 557

[56] References Cited

U.S. PATENT DOCUMENTS

| | | | |
|---|---|---|---|
| 3,471,582 | 10/1969 | Lupfer | 260/677 |
| 3,656,911 | 4/1972 | Hobbs | 422/62 |

*Primary Examiner*—R. E. Serwin

[57] ABSTRACT

A selective hydrogenation process wherein at least two catalyst beds in series is controlled by predicting the inlet temperature to the first catalyst bed in the series required to maintain the concentration of the component being selectively hydrogenated in the effluent flowing from the second reactor within a desired concentration limit. This prediction is biased by a comparison of the actual concentration to the concentration limit. The thus biased prediction is utilized to manipulate the inlet temperature to the first reactor in the series. The inlet temperature to the second reactor to the series is controlled by establishing a prediction of the differential temperature across the second reactor in the series. The predicted differential temperature is compared to the actual differential temperature and the results of the comparison is utilized to control the inlet temperature to the second reactor in the series so as to maintain a desired relationship between the amount of the impurity selectively hydrogenated in the first catalyst bed and the amount of the impurity selectively hydrogenated in the second catalyst bed.

11 Claims, 2 Drawing Figures

TEMPERATURE CONTROL OF EXOTHERMIC REACTIONS

This invention relates to temperature control of an exothermic reaction. In a specific aspect, this invention relates to selective hydrogenation of unsaturated hydrocarbons in mixed hydrocarbon streams. In another specific aspect, this invention relates to selective hydrogenation of acetylenic compounds in olefin rich hydrocarbon streams. In still another aspect, this invention relates to method and apparatus for controlling a selective hydrogenation process so as to maintain the concentration of the impurity being selectively hydrogenated within required limits. In still another specific aspect, this invention relates to method and apparatus for controlling a selective hydrogenation process wherein at least two catalyst beds in series are utilized so as to maintain a desired relationship between the amount of the impurity selectively hydrogenated in the first catalyst bed and the amount of the impurity selectively hydrogenated in the second catalyst bed.

In many exothermic chemical reactions, it is necessary to control temperature within certain limits in order to maintain satisfactory yields and to prevent side reactions. This is particularly true in selective hydrogenation processes. For example, ethylene is commonly produced by the thermocracking of hydrocarbon feedstocks. Unfortunately, some acetylene is also produced, and must be removed for many applications. This can be accomplished by selective catalytic hydrogenation of the acetylene.

In selective hydrogenation operations of this type, it is quite important to maintain the operating temperature within narrow limits. If the temperature is too low, the hydrogenation reaction is not carried out in a sufficiently complete manner to remove the acetylene. If the temperature becomes too high, side reactions such as the hydrogenation of ethylene and the formation of polymers may result. It is also very important to prevent excessive temperatures from being reached because of the danger of explosions.

It is also important where two catalyst beds or reaction zones in series are utilized as in the present invention, to maintain a relationship between the percentage of the acetylene hydrogenated in the first catalyst bed and the percentage of the acetylene hydrogenated in the second catalyst bed. Preferably, the first catalyst bed is utilized to hydrogenate most of the acetylene with the second catalyst bed being utilized primarily as a clean-up process. Close control of the percentage of the acetylene hydrogenated in each catalyst bed provides a more efficient conversion of acetylene and reduces the risk of excessive temperature in either catalyst bed.

It is thus an object of this invention to provide method and apparatus for controlling the reaction temperature of an exothermic chemical reaction process. Another object of this invention is to provide method and apparatus for controlling the selective hydrogenation of unsaturated hydrocarbons in mixed hydrocarbon streams. Still another object of this invention is to provide method and apparatus for controlling the selective hydrogenation of acetylenic compounds in olefin rich hydrocarbon streams. Still another object of this invention is to provide method and apparatus for controlling a selective hydrogenation process so as to maintain the concentration of the impurity being hydrogenated within required limits. Still another object of this invention is to provide method and apparatus for controlling a selective hydrogenation process so as to maintain a desired relationship between the amount of the impurity selectively hydrogenated in the first catalyst bed and the amount of the impurity selectively hydrogenated in the second catalyst bed.

In accordance with the present invention, a selective hydrogenation process which utilizes two catalyst beds or reaction zones in series is controlled so as to maintain a desired concentration of the impurity being selectively hydrogenated in the effluent flowing from the second catalyst bed in the series. The selective hydrogenation process is also controlled so as to maintain a desired relationship between the amount of material selectively hydrogenated in the first catalyst bed and the amount of material selectively hydrogenated in the second catalyst bed. Two separate reactors may be utilized or a single reactor with two catalyst beds may be utilized so long as control and a temperature measurement of the fluid stream flowing between the two catalyst beds is possible. Hereafter, the term first reactor and second reactor is utilized to describe the invention but the invention is not limited to the use of separate reactor vessels.

The feedstream to the first reactor and the feedstream from the first reactor to the second reactor are split into at least two portions. A first portion of the feedstream to the first reactor is heated before being passed to the first reactor. A second portion of the feedstream to the first reactor is utilized as a quench fluid and is introduced into the first portion of the feedstream to the first reactor after the first portion of the feedstream to the first reactor has been heated. A first portion of the feedstream from the first reactor to the second reactor is supplied directly to the second reactor. A second portion of the feedstream from the first reactor to the second reactor is cooled and is utilized as a quench fluid by being introduced into the first portion of the feedstream from the first reactor to the second reactor before the feedstream enters the second reactor.

An analysis of the feedstream flowing to the first reactor is utilized to provide an indication of the amount of acetylene in the feedstream and also an indication of the amount of carbon monoxide in the feedstream. Based on this analysis, a measurement of the flow rate of the feedstream flowing to the first reactor, and the set point for the concentration of acetylene in the effluent flowing from the second reactor, a signal representative of a prediction of the inlet temperature for the first reactor required to maintain the concentration of the acetylene in the effluent flowing from the second reactor equal to a desired concentration is established. This prediction is biased by a comparison of the actual acetylene concentration in the effluent flowing from the second reactor to the acetylene concentration limit for the effluent flowing from the second reactor to provide a corrected prediction of the inlet temperature for the first reactor required to maintain the acetylene concentration in the effluent flowing from the second reactor equal to a desired concentration. This corrected prediction is compared to the actual inlet temperature of the first reactor and the results of the comparison is utilized to manipulate the inlet temperature for the first reactor so as to maintain the concentration of the acetylene in the effluent flowing from the outlet of the second reactor substantially equal to the desired concentration of the acetylene.

A prediction of the differential temperature across the second reactor which is required to maintain the desired ratio between the differential temperature across the second reactor and the differential temperature across the first reactor is also established. This predicted differential temperature is compared to the actual differential temperature and the inlet temperature to the second reactor is manipulated in response to the results of the comparison. This ensures that the ratio of the differential temperature across the second reactor to the differential temperature across the first reactor is substantially equal to a ratio set point which will maintain a desired relationship between the amount of material selectively hydrogenated in the first catalyst bed and the amount of material selectively hydrogenated in the second catalyst bed.

In this manner, the required reaction temperatures are maintained in each reactor so as to maintain the concentration of the acetylene in the effluent flowing from the second reactor substantially equal to the desired concentration for the acetylene in the effluent flowing from the second reactor. Also, a desired relationship between the amount of the acetylene hydrogenated in the first reactor and the amount of the acetylene hydrogenated in the second reactor is maintained.

Figure 2:
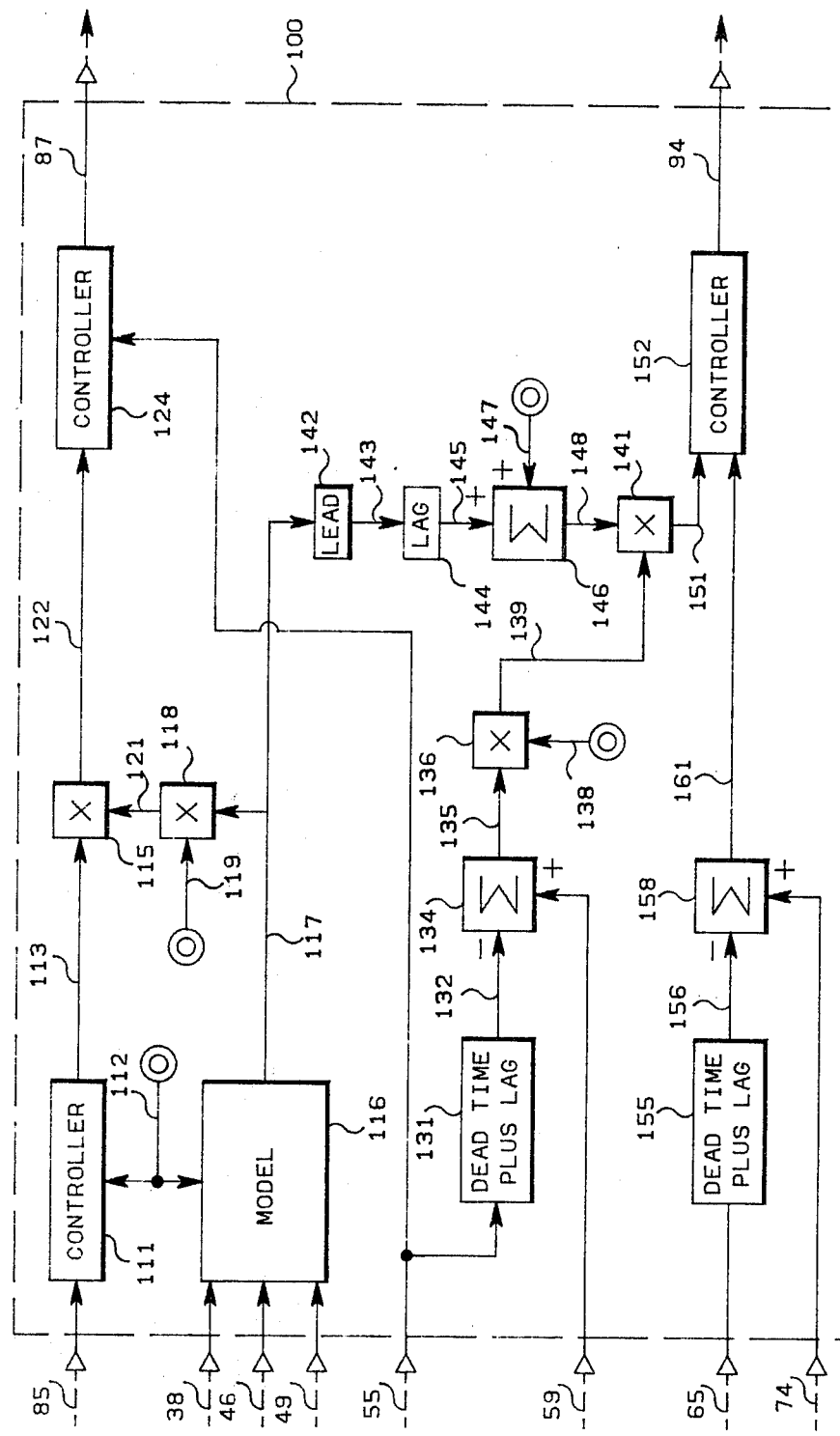

Other objects and advantages of the invention will be apparent from the foregoing brief description of the invention and the appended claims as well as from the detailed description of the drawings in which:

FIG. 1 is a schematic diagram of a selective hydrogenation process with an associated control system; and FIG. 2 is a logic diagram of the computer logic utilized to generate the control signals utilized in the control of the selective hydrogenation process illustrated in FIG. 1.

The invention is illustrated and described in terms of a selective hydrogenation process for the hydrogenation of acetylene in an ethylene product. However, it should be understood that this invention can be utilized for carrying out other selective hydrogenation processes such as the conversion of diolefins to olefinic and/or saturated compounds.

Although the invention is illustrated and described in terms of a specific hydrogenation process, the applicability of the invention described herein extends to other process configurations such as using different heat exchanger configurations, more than two reactors or, as has been previously stated, two catalyst beds in a single reactor vessel. The invention also extends to different types of control system configurations which accomplish the purpose of the invention. Lines designated as signal lines in the drawing are either pneumatic or electrical in this preferred embodiment. However, this invention is also applicable to mechanical, hydraulic or other signal means for transmitting information. In many control systems, some combination of these types of signals will be used. However, use of any other type of signal transmission, compatible with the process and equipment in use, is within the scope of the invention.

A digital computer is used in the preferred embodiment of this invention to calculate the required control signals based on measured process parameters as well as set points supplied to the computer. Analog computers or other types of computing devices could also be used in the invention.

The digital controllers shown may utilize the various modes of control such as proportional, proportional-integral, proportional-derivative, or proportional-integral-derivative. In this preferred embodiment, proportional-integral controllers are utilized but any controller capable of accepting two input signals and producing a scaled output signal, representative of a comparison of the two input signals, is with the scope of the invention. The operation of proportional-integral controllers is well known in the art. The output control signal of a proportional-integral controller may be represented as $$S = K_1 E + K_2 \int E dt$$

where
$S$ = output control signals;
$E$ = difference between two input signals; and
$K_1$ and $K_2$ = constants.

The scaling of an output signal by a controller is well known in control systems art. Essentially, the output of a controller may be scaled to represent any desired factor or variable. An example of this is where a desired temperature and an actual temperature is compared by a controller. The output could be a signal representative of a desired change in the flow rate of some fluid necessary to make the desired and actual temperatures equal. On the other hand, the same output signal could be scaled to represent a percentage or could be scaled to represent a pressure change required to make the desired and actual temperatures equal. If the controller output can range from binary 0 to binary 10, then the output signal could be scaled so that an output signal having a value of a binary 5 corresponds to 50 percent, some specified flow rate, or some specified pressure.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. In addition, all signals could be translated into a "suppressed zero" or other similar format in order to provide a "live zero" and prevent an equipment failure from being erroneously interpreted as a "low" or "high" measurement or control signal. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to the drawings, and in particular FIG. 1, an ethylene feedstream containing some concentration of acetylene and carbon monoxide is introduced through conduit means 8, 9 and 10 to the reactor 12 which contains a first catalyst bed containing a hydrogenation catalyst. Heat exchanger 14 is operably located between conduit means 9 and 10. Steam or other suitable heating fluid is provided through conduit means 17 to the heat exchanger 14 and is utilized to provide heat to the feed flowing through conduit means 8, 9, and 10. Pneumatic control valve 21 is operably located in conduit means 8 and is utilized to split the flow of the feed between conduit means 9 and the bypass conduit means 11. The feed flowing through conduit means 10 and the bypass conduit means 11 are preferably mixed before the feed enters the reactor 12. The feed flowing through the bypass conduit means 11 is utilized as a quench fluid to provide further temperature control of the feed flowing to the reactor 12.

The effluent flowing from the reactor 12 is passed through conduit means 22 and 23 to the reactor 18, which contains a second catalyst bed containing the hydrogenation catalyst. Heat exchanger 25, which is operably located between conduit means 22 and 23, is utilized to provide a means for cooling the effluent flowing through conduit means 22 and 23. A cooling fluid, such as water, is provided through conduit means 26 to the heat exchanger 25. The pneumatic control valve 28, which is operably located in conduit means 22, is utilized to control the relationship between the amount of effluent flowing from the reactor 12, which flows to the reactor 18 through the heat exchanger 25 and through the bypass conduit means 24. The effluent flowing through conduit means 24 may be considered the primary effluent stream and the effluent flowing through conduit means 22, the heat exchanger 25, and conduit means 23 may be considered the quench fluid stream. The two fluid streams flowing through conduit means 24 and conduit means 23 are preferably mixed before entering the reactor 18.

The ethylene product, which will have a very low concentration of acetylene, is removed from the reactor 18 through conduit means 19. The product removed from the reactor 18 through conduit means 19 is generally provided to other portions of the ethylene manufacturing process.

The selective hydrogenation process described to this point is a conventional selective hydrogenation process. It is the manner in which the selective hydrogenation process, illlustrated in FIG. 1, is controlled so as to maintain a desired concentration of acetylene in the product flowing from the reactor 18 through conduit means 19 and to maintain a desired relationship between the amount of the impurity selectively hydrogenated in the first catalyst bed and the amount of the impurity selectively hydrogenated in the second catalyst bed which provides the novel features of the present invention.

Control of the selective hydrogenation process illustrated in FIG. 1 is generally accomplished by measuring a plurality of system parameters and supplying the measured parameters to computer means 100. Computer means 100 is preferably an Optrol 3600 manufactured by Applied Automation, Inc., Bartlesville, Okla. Computer means 100 is also supplied with a plurality of set point signals which are representative of desired operating characteristics for the selective hydrogenation process illustrated in FIG. 1. In response to the measured inputs and the set point inputs, computer means 100 calculates the temperature of the feedstream flowing to the reactor 12 required to maintain a desired concentration of acetylene in the bottom product flowing from the reactor 18 through conduit means 19. Computer means 100 also calculates the temperature of the feedstream flowing to the reactor 18 required to maintain a desired relationship between the amount of the acetylene selectively hydrogenated in reactor 12 and the amount of the acetylene selectively hydrogenated in reactor 18.

Flow transducer 31, in combination with the flow sensor 32 which is operably located in conduit means 8, provides an output signal 34 which is representative of the flow rate of the feed flowing through conduit means 8. Signal 34 is provided from the flow transducer 31 to the pressure to current (P/I) transducer 35. Signal 34 is converted from pneumatic form to electrical form by the P/I transducer 35 and is provided as signal 36 to the analog to digital (A/D) converter 37. Signal 36 is converted from analog form to digital form by the A/D converter 37 and is provided as signal 38 to computer means 100.

Analyzer transducer 41, which is operably connected to conduit means 8, provides a pair of output signals 42 and 43. Signal 42, which is representative of the concentration of acetylene in the feedstream flowing through conduit means 8, is provided from the analyzer transducer 41 to the A/D converter 45. Signal 42 is converted from analog form to digital form and is provided as signal 46 to computer means 100. Signal 43, which is representative of the concentration of carbon monoxide in the feedstream flowing through conduit means 8, is provided from the analyzer transducer 41 as an input to the A/D converter 47. Signal 43 is converted from analog form to digital form and is provided as signal 49 to computer means 100.

Temperature transducer 51, in combination with a temperature measuring device such as a thermocouple which is operably located in conduit means 10, provides an output signal 52 which is representative of the temperature of the effluent flowing through conduit means 10 into the reactor 12. Signal 52 is provided from the temperature transducer 51 to the A/D converter 53. Signal 52 is converted from analog form to digital form and is provided as signal 55 to computer means 100.

Temperature transducer 56, in combination with a temperature measuring device such as a thermocouple which is operably located in conduit means 22, provides an output signal 57 which is representative of the temperature of the effluent flowing through conduit means 22 out of the reactor 12. Signal 57 is provided from the temperature transducer 56 to the A/D converter 58. Signal 57 is converted from analog form to digital form and is provided as signal 59 to computer means 100.

Temperature transducer 61, in combination with a temperature measuring device such as a thermocouple which is operably located in conduit means 23, provides an output signal 62 which is representative of the temperature of the effluent flowing through conduit means 23 into the reactor 18. Signal 62 is provided from the temperature transducer 61 to the A/D converter 64. Signal 62 is converted from analog form to digital form by A/D converter 64 and is provided as signal 65 to computer means 100.

Temperature transducer 71, in combination with a temperature measuring device such as a thermocouple which is operably located in conduit means 19, provides an output signal 72 which is representative of the temperature of the product flowing through conduit means 19. Signal 72 is provided from the temperature transducer 71 as an input to the A/D converter 73. Signal 72 is converted from analog form to digital form by the A/D converter 73 and is provided as signal 74 to computer means 100.

Analyzer transducer 81, which is operably connected to conduit means 19, provides an output signal 83 which is representative of the concentration of the acetylene in the product flowing through conduit means 19. Signal 83 is provided from the analyzer transducer 81 as an input to the A/D converter 84. Signal 83 is converted from analog form to digital form and is provided as signal 85 to computer means 100.

In response to the described inputs and a plurality of set point inputs, computer means 100 calculates two control signals which are utilized in controlling the selective hydrogenation process illustrated in FIG. 1. One control signal 87, calculated by computer means 100, is representative of the setting of the pneumatic control valve 21 required to maintain the concentration of the acetylene in the product flowing through conduit means 19 substantially equal to a desired concentration. Signal 87 is provided from computer means 100 to the digital to analog (D/A) converter 88. Signal 87 is converted from digital form to analog form and is provided as signal 89 to the current to pressure (I/P) transducer 90. Signal 89 is converted from electrical form to pneumatic form by the I/P transducer 90 and is provided as signal 92 to the pneumatic control valve 21. The pneumatic control valve 21 is manipulated in response to signal 92 to thereby maintain the temperature of the feed flowing to the reactor 12 substantially equal to the desired temperature represented by signal 89.

A second control signal 94, calculated by computer means 100, is representative of the setting of the pneumatic control valve 28 required to maintain the ratio of the temperature differential across reactor 18 to the temperature differential across reactor 12 substantially equal to a desired ratio. Signal 94 is provided from computer means 100 to the D/A converter 95. Signal 94 is converted from digital form to analog form and is provided as signal 96 to the I/P transducer 97. Signal 96 is converted from electrical form to pneumatic form and is provided as signal 98 to the pneumatic control valve 28. The pneumatic control valve 28 is manipulated in response to signal 98 so as to maintain the actual temperature of the feed flowing to reactor 18 substantially equal to the desired temperature represented by signal 94.

The logic flow diagram utilized to calculate the control signals 87 and 94 in response to the previously described input signals to computer means 100 and in response to set point signals provided to computer means 100 is illustrated in FIG. 2. Referring now to FIG. 2, signal 85, which is representative of the acetylene concentration in the product flowing through conduit means 19 is provided as an input to the controller block 111, which is a digital implementation of a proportional-integral controller. The controller block 111 is also provided with a set point signal 112, which is representative of the desired concentration of acetylene in the product flowing through conduit means 19. In response to signals 85 and 112, the controller 111 provides an output signal 113, which is responsive to the difference between signals 85 and 112. Signal 113 is provided from the controller block 111 to the multiplying block 115.

Signals 38, 46, and 49, which are representative of the flow rate of the feed, concentration of acetylene in the feed and concentration of carbon monoxide in the feed flowing through conduit means 8, respectively, are provided as inputs to the model block 116. The set point signal 112 is also provided as an input to the model block 116. In response to the described inputs, the model block 116 provides an output signal 117 which is a prediction of the temperature of the feed flowing to the reactor 12 required to maintain the acetylene concentration in the product flowing through conduit means 19 substantially equal to the desired concentration represented by signal 112. The manner in which signal 117 is derived in the model block 116 is as follows.

In general, the average temperature across an acetylene reactor is given by the known relationship $$T_{AVG} = \text{function} \frac{C_1}{\ln C_2 X_H - \ln X_o^2 F - \ln B} \quad \text{(I)}$$

where
$T_{AVG}$ = average temperature across the acetylene reactor,
$X_o$ = concentration of carbon monoxide in the feedstream,
$X_H$ = concentration of hydrogen in the feedstream,
$B = \ln(X_{A\ in}/X_{A\ out\ SP})$,
$X_{A\ in}$ = acetylene concentration in the feed,
$X_{A\ out\ SP}$ = desired acetylene concentration in the product from the reactor,
and $C_1$ and $C_2$ are constants.

Assuming that a large volume of hydrogen will be present in the acetylene reactor and rearranging Equation 1 gives $$T_{AVG} = \frac{C_1}{C_3 - \ln F - 2\ln X_o - \ln B} \quad \text{(II)}$$

wherein $C_3$ is a constant and $C_1$, $F$, $X_o$ and $B$ are as previously defined.

The inlet temperature to the acetylene reactor will generally be lower than the average temperature across the reactor. However, the average temperature across the reactor can be utilized to give an approximation of the inlet temperature required to maintain the acetylene concentration set point ($X_{A\ out\ SP}$) at a desired value. Thus, for the purpose of the present invention, $T_{AVG}$ of equation II is utilized as a prediction of the temperature of the feed flowing to reactor 12 required to maintain the actual concentration of the acetylene in the product flowing through conduit means 19 substantially equal to the desired concentration of the acetylene flowing through conduit means 19.

The constants $C_1$ and $C_3$ are generally obtained from operating data by curve fitting. However, the constants $C_1$ and $C_3$ may be obtained from published literature or from reaction rates if desired. Equation II is solved in the model block 116 to provide signal 117 in response to the described inputs to the model block 116.

Signal 117 is provided from the model block 116 as an input to the multiplying block 118 and is also provided as an input to the lead block 142. The multiplying block 118 is also provided with a bias term 119 which will generally be representative of 1.0. Signal 118 is multiplied by signal 119 to establish signal 121 which is provided as an input to the multiplying block 115. Signal 119 may be utilized to bias signal 117 if it is determined that the use of a constant bias term to bias signal 117 provides a better result than is provided by the use of the model 116 alone.

Signal 121 is considered a prediction of the temperature of the feed flowing to the inlet of reactor 12 required to maintain a desired concentration of acetylene in the product flowing through conduit means 19. Signal 113 is utilized as a feedback bias term. Signal 121 is multiplied by signal 113 to provide signal 122 which is a corrected prediction of the temperature of the feed flowing to the inlet of reactor 12 required to maintain a desired concentration of acetylene in the product flowing through conduit means 19. Signal 122 is provided as a set point signal to the controller block 124, which is a digital implementation of a proportional-integral-controller. The controller block 124 is also provided with signal 55 which is representative of the actual temperature of the feed flowing to the inlet of reactor 12. In response to signals 55 and 122, the controller 124 provides signal 87, which is responsive to the difference between signals 55 and 122. Signal 87 is provided as an output control signal from computer means 100 and is utilized as has been previously described.

Signal 55 is also provided as an input to the dead time plus lag block 131. The dead time is the time required for a step change of the inlet temperature to reactor 12 to effect the outlet temperature of the effluent flowing from reactor 12. The lag is the time from when the outlet temperature of the reactor 12 first changed until the outlet temperature of the reactor 12 again reaches steady state. The dead time for a typical acetylene reactor is about 15 minutes. The lag for a typical acetylene reactor is about 10 minutes. However, it is noted that both dead time and lag is a function of the feed rate to the reactor so the typical times will change with various feed rates. The output signal 132 from the dead time plus lag block 131 is representative of signal 55 delayed by the time represented by the dead time and the lag. Signal 132 is provided from the dead time plus lag block 131 to the subtrahend input of the summing block 134. Signal 59, which is representative of the outlet temperature of the reactor 12, is provided to the minuend input of the summing block 134. Signal 132 is subtracted from signal 59 to provide signal 135, which is representative of the temperature differential across the reactor 12 compensated by the dead time and lag of the dead time plus lag block 131. Signal 135 is provided from the summation block 134 to the multiplying block 136. The multiplying block 136 is also provided with a set point signal 138 which is representative of the desired ratio of the differential temperature across reactor 18 to the differential temperature across reactor 12. Signal 135 is multiplied by signal 138 to provide signal 139, which is representative of a prediction of the differential temperature across reactor 18 required to maintain the desired ratio of the differential temperature across reactor 18 to the differential temperature across reactor 12. Signal 139 is provided from the multiplying block 136 as an input to the multiplying block 141.

The lead block 142 is utilized to change the inlet temperature to reactor 18 when there is a feed composition change or a feed rate change to reactor 12. This is done to maintain the desired acetylene concentration in the product flowing through conduit means 19. Since the inlet temperature to reactor 12 will be changed in response to a change in the feed composition or the feed rate, the temperature profile across reactor 12 will change over a period of time in response to a change in the feed composition or feed rate until the reactor 12 again reaches a steady state operation. As the temperature profile across reactor 12 changes, the quantity of acetylene in the effluent flowing from the reactor 12 will also change. Thus, the inlet temperature to reactor 18 is changed by the lead block 142 to compensate for changes in the temperature profile across reactor 12. The lead block 142 will make a change in the reactor 18 inlet temperature. The output signal 143 from the lead block 142 is supplied to the lag block 144 which is utilized to remove the change as reactor 12 comes to steady state operation again.

The equation utilized to calculate the lead time is $$Y = X + (LT/SI)*(X - XP) \qquad \text{III}$$

where
  Y = the value of signal 144 which is provided from the lead lag netword 142,
  X = the value of signal 55,
  XP = a previous value of signal 55,
  LT = lead time constant, and
  SI = sample interval.

The lag time equation is $$FV = FVP + (SI/TC)*(IN - FVP) \qquad \text{IV}$$

where
  FV the output signal 144,
  FVP = previous value for signal 144,
  SI = sample interval,
  TC = time constant, and
  IN = the value of signal 55.

The output signal 145 from the lag block 144 is supplied to the summing block 146. The summing block 146 is also provided with a bias signal 147 which is representative of 1.0. The bias signal 147 is provided simply to ensure that the signal provided to the multiplying block 141 will not be to 0. The bias signal 147 is added to signal 145 to establish signal 148 which is provided to the multiplying block 141. It is noted that the value of signal 145 will be 0 when signal 87 is substantially constant and thus signal 148 will be equal to 1.0 unless the set point for the inlet temperature to reactor 12 is changing. If the set point for the inlet temperature to reactor 12 is changing, signal 148 is utilized to bias signal 139 to compensate for changes in the set point for the imminent temperature to reactor 12 and the effect of these changes on the prediction of the differential temperature across reactor 18. Signal 139 is multiplied by signal 148 to establish signal 151 which is representative of the corrected prediction of the differential temperature across the reactor 18 required to maintain the desired ratio of the differential temperature across reactor 18 to the differential temperature across reactor 12. Signal 148 effectively compensates for changes in the feed rate or feed composition. Signal 151 is provided from the multiplying block 141 to the controller block 152 which is a digital implementation of a proportional-integral controller.

Signal 65 which is representative of the teemperature of the feed flowing to reactor 18 is provided as an input to the dead time plus lag block 155. The dead time plus lag block 155 is the time as the dead time plus lag block 131 except that the dead time is for reactor 18 and the lag is for reactor 18. The dead time would typically be 15 minutes for reactor 18 and the lag will be typically 6 minutes for reactor 18.

Signal 156 which is provided as an output from the dead time plus lag block 155 will thus be representative of signal 65 delayed by the dead time and the lag. Signal 156 is provided from the dead time plus lag block 155 to the subtrahend input of the summing block 158.

Signal 74, which is representative of the temperature of the product flowing from the reactor 18, is provided to the minuend input of the summing block 158. Signal 156 is subtracted from signal 74 to provide signal 161 which is representative of the actual differential temperature across the reactor 18. Signal 161 is provided from the summing block 158 as an input to the controller 152. In response to signals 151 and 161, the controller 152 provides the output signal 94 which is responsive to the difference between signals 161 and 151. Signal 94 is provided as an output from computer means 100 and is utilized as previously described.

The control system illustrated in FIGS. 1 and 2 provides both feedforward and feedback control of the temperature of the feedstream flowing to the reactor 12 and the temperature of the feedstream flowing to the reactor 18. Feedforward control of the temperature of the feedstream flowing to the reactor 12 is provided by the model 116. Feedback control of the temperature of the feed flowing to the reactor 12 is provided by the bias term 113 which is generated in response to a comparison of the actual acetylene concentration in the product flowing through conduit means 19 and the desired concentration of the acetylene in the product flowing through conduit means 19. The feedforward control of the temperature of the feed flowing to the reactor 18 is provided by the prediction of the differential temperature across the reactor 18 as corrected by the feedforward control for reactor 12. Feedback control of the inlet temperature to the reactor 18 is provided by a comparison of the actual differential temperature across the reactor 18 to the corrected predicted required differential temperature across the reactor 18.

The combination of feedforward and feedback control allows close control of the acetylene concentration specification for the product stream flowing to conduit means 19 and also allows close control of the ratios of the differential temperatures across the two reactors so as to insure that a desired relationship between the amount of the acetylene selectively hydrogenated in reactor 18 and the amount of the acetylene selectively hydrogenated in reactor 18 is maintained.

The invention has been described in terms of a preferred embodiment as illustrated in FIGS. 1 and 2. Specific components utilized in the practice of the invention as illustrated in FIG. 1 such as flow sensor 32; flow transducer 31; pneumatic control valves 21 and 28; temperature transducers 51, 56, 61 and 71; pressure to current transducer 35; and current to pressure transducers 90 and 97 are each well known, commercially available control components such as are described at length in Perry's Chemical Engineer's Handbook, 4th Ed., Chapter 22, McGraw Hill. Other components not previously specified are as follows:

| | |
|---|---|
| A/D converters 37, 45, 47, 53, 58, 64, 73, and 84 | MM 5357, 8 bit, A/D converter, National Semiconductor; |
| D/A converters 95 and 88 | AD 559, 8 bit, D/A converter, Analog Devices; |
| Analyzer transducers 41 and 81 | 102 Process Chromatograph System Applied Automation, Inc. Bartlesville, Oklahoma. |

For reasons of brevity, conventional auxiliary equipment commonly used in selective hydrogenation processes such as pumps, heat exchangers, additional measurement dash control devices, etc. have not been included in the above description as they play no part in the explanation of the invention.

While the invention has been described in terms of the presently preferred embodiments, reasonable variations and modificiations within the scope of the described invention and the appended claims are possible by those skilled in the art. Variations such as using an analog computer to perform the required calculations are within the scope of the invention. Other variations, such as having two catalyst beds in a single reactor, are within the scope of the invention as long as the temperature of the feed stream flowing between the two catalyst beds can be measured and control can be exerted over the temperature of the feedstream flowing between the two catalyst beds.

That which is claimed is:

1. Apparatus comprising:

a first catalyst bed;

means for supplying a first feedstream containing a first constituent to said first catalyst bed, a portion of said first constitutent in said first feedstream being removed from said first feedstream in said first catalyst bed;

a second catalyst bed;

means for withdrawing the reaction effluent from said first catalyst bed as a first product stream and for supplying said first product stream as a second feedstream to said second catalyst bed, a portion of said first constituent in said second feedstream being removed from said second feedstream in said second catalyst bed;

means for withdrawing the reaction effluent, containing a substantially reduced concentration of said first constituent, from said second catalyst bed as a second product stream;

means for establishing a first signal representative of a prediction of the temperature of said first feedstream required to maintain a desired concentration of said first constituent in said second product stream;

means for establishing a second signal representative of the actual concentration of said first constituent in said second product stream;

means for establishing a third signal representative of the desired concentration of said first constituent in said second product stream;

means for comparing said second signal and said third signal and for establishing a fourth signal responsive to the difference between said second signal and said third signal;

means for biasing said first signal with said fourth signal to produce a fifth signal representative of a corrected prediction of the temperature of said first feedstream required to maintain the desired concentration of said first constituent in said second product stream;

means for manipulating the temperature of said first feedstream in response to said fifth signal;

means for establishing a sixth signal representative of the prediction of the differential temperature across said second catalyst bed required to maintain the ratio of the differential temperature across said second catalyst bed to the differential temperature across said first catalyst bed substantially equal to a desired ratio of the differential temperature across said second catalyst bed to the differential temperature across said first catalyst bed;

means for establishing a seventh signal representative of the temperature of said second feedstream;

means for establishing an eighth signal representative of the temperature of said second product stream;

means for comparing said seventh signal and said eighth signal and for establishing a ninth signal responsive to the difference between said seventh signal and said eighth signal;

means for comparing said sixth signal and said ninth signal and for establishing a tenth signal responsive to the difference between said sixth signal and said ninth signal; and means for manipulating the temperature of said second feedstream in response to said tenth signal.

2. Apparatus in accordance with claim 1 wherein said means for establishing said first signal comprises:

means for establishing an eleventh signal representative of the feed rate of said first feedstream;

means for establishing a twelfth signal representative of the concentration of said first constituent in said first feedstream;

means for establishing a thirteenth signal representative of the concentration of a second constituent in said first feedstream, said second constituent being a constituent which tends to poison the catalyst in said first and second catalyst beds; and means for establishing said first signal in response to said eleventh, twelfth, thirteenth, and third signals.

3. Apparatus in accordance with claim 2 wherein said means for biasing said first signal with said fourth signal comprises:

means for multiplying said first signal by said fourth signal.

4. Apparatus in accordance with claim 3 wherein said means for controlling the temperature of said first feedstream in response to said fifth signal comprises:

means for establishing a fourteenth signal representative of the actual temperature of said first feedstream;

means for comparing said fifth signal and said fourteenth signal and for establishing a fifteenth signal responsive to the difference between said fifth signal and said fourteenth signal; and means for manipulating the temperature of said first feedstream in response to said fifteenth signal.

5. Apparatus in accordance with claim 1 wherein said means for establishing said sixth signal comprises:

means for establishing an eleventh signal representative of the temperature of said first feedstream;

means for delaying said eleventh signal to establish a twelfth signal, the delay being substantially equal to the time required for a step change in the temperature of said first feedstream to effect the temperature of said first product stream plus the time required for the temperature of said first product stream to reach a substantially steady state condition after a change first occurs in the temperature of said first product stream;

means for establishing a thirteenth signal representative of the temperature of said first product stream;

means for subtracting said twelfth signal from said thirteenth signal to establish a fourteenth signal representative of the differential temperature across said first catalyst bed;

means for establishing a fifteenth signal representative of the desired ratio of the differential temperature across said second catalyst bed to the differential temperature across said first catalyst bed;

means for multiplying said fourteenth signal by said fifteenth signal to establish a sixteenth signal representative of a prediction of the differential temperature across said second catalyst bed which will maintain the desired ratio of the differential temperature across said second catalyst bed to the differential temperature across said first catalyst bed;

means for biasing said sixteenth signal with said first signal to establish said sixth signal.

6. Apparatus in accordance with claim 5 wherein said means for biasing said sixteenth signal with said first signal comprises:

a lead means;

means for supplying said first signal as an input to said lead means to thereby establish a seventeenth signal;

a lag means;

means for supplying said seventeenth signal as an input to said lag means to thereby establish an eighteenth signal; and means for multiplying said eighteenth signal by said sixteenth signal.

7. A method for removing a first constituent in a feed stream, wherein said feed stream is supplied to the first of two reaction zones in series, comprising the steps of:

establishing a first signal representative of a prediction of the temperature of said feedstream required to maintain a desired concentration of said first constituent in the product stream flowing from the second one of said two reaction zones in series;

establishing a second signal representative of the actual concentration of said first constituent in said product stream;

establishing a third signal representative of the desired concentration of said first constituent in said product stream;

comparing said second signal and said third signal and establishing a fourth signal responsive to the difference between said second signal and said third signal;

biasing said first signal with said fourth signal to produce a fifth signal representative of a corrected prediction of the temperature of said feedstream required to maintain the desired concentration of said first constituent in said product stream;

manipulating the temperature of said feedstream in response to said fifth signal;

establishing a sixth signal representative of a prediction of the differential temperature across the second one of said two reaction zones in series required to maintain the ratio of the differential temperature across the second one of said two reaction zones in series to the differential temperature across the first one of said two reaction zones in series substantially equal to a desired ratio of the differential temperature across the second one of said two reaction zones in series to the differential temperature across the first one of said two reaction zones in series;

establishing a seventh signal representative of the temperature of the effluent stream flowing from the first one of said two reaction zones in series to the second one of said two reaction zones in series;

establishing an eighth signal representative of the temperature of said product stream;

comparing said seventh signal and said eighth signal and establishing a ninth signal responsive to the difference between said seventh signal and said eighth signal;

comparing said sixth signal to said ninth signal and establishing a tenth signal responsive to the difference between said sixth signal and said ninth signal; and manipulating the temperature of said effluent stream in response to said tenth signal.

8. A method in accordance with claim 7 wherein said step of establishing said first signal comprises:

establishing an eleventh signal representative of the feed rate of said feedstream;

establishing a twelfth signal representative of the concentration of said first constituent in said feedstream;

establishing a thirteenth signal representative of the concentration of a second constituent in said feedstream, said second constituent being a constituent which tends to poison the catalyst in said two reaction zones; and establishing said first signal in response to said eleventh, twelfth, thirteenth, and third signals.

9. A method in accordance with claim 8 wherein said step of biasing said first signal with said fourth signal comprises multiplying said first signal by said fourth signal.

10. A method in accordance with claim 9 wherein said step of controlling the temperature of said feedstream in response to said fifth signal comprises:

establishing a fourteenth signal representative of the actual temperature of said feedstream;

comparing said fifth signal and said fourteenth signal and establishing a fifteenth signal responsive to the difference between said fifth signal and said fourteenth signal; and manipulating the temperature of said feedstream in response to said fifteenth signal.

11. A method in accordance with claim 7 wherein said step of establishing said sixth signal comprises:

establishing an eleventh signal representative of the temperature of said feedstream;

delaying said eleventh signal to establish a twelfth signal, the delay being substantially equal to the time required for a step change in the temperature of said feedstream to effect the temperature of said effluent stream plus the time required for the temperature of said effluent stream to reach a substantially steady state condition after a change first occurs in the temperature of said effluent stream;

establishing a thirteenth signal representative of the temperature of said effluent stream;

subtracting said twelfth signal from said thirteenth signal to establish a fourteenth signal representative of the differential temperature across the first one of said two reaction zones in series;

establishing a fifteenth signal representative of the desired ratio of the differential temperature across the second one of said two reaction zones in series to the differential temperature across the first one of said two reaction zones in series;

multiplying said fourteenth signal by said fifteenth signal to establish a sixteenth signal representative of a prediction of the differential temperature across the second one of said two reaction zones in series which will maintain the desired ratio of the differential temperature across the second one of said two reaction zones in series to the differential temperature across the first one of said two reaction zones in series;

biasing said sixteenth signal with said first signal to establish said sixth signal.

* * * * *